United States Patent [19]

Shiozaki

[11] Patent Number: 4,696,306
[45] Date of Patent: Sep. 29, 1987

[54] ELECTROCARDIOGRAM PLAYBACK SYSTEM AND METHOD

[75] Inventor: Yoshihiko Shiozaki, Tokyo, Japan

[73] Assignee: Akai Electric Co., Ltd., Tokyo, Japan

[21] Appl. No.: 932,528

[22] Filed: Nov. 20, 1986

[30] Foreign Application Priority Data

Nov. 20, 1985 [JP] Japan .................................. 60-262017

[51] Int. Cl.⁴ .......................... A61B 5/04; G01D 9/00
[52] U.S. Cl. .................................... 128/711; 128/696; 128/710; 346/33 ME
[58] Field of Search ............... 128/696, 706, 710, 711, 128/712; 346/33 ME, 33 M; 360/8

[56] References Cited

U.S. PATENT DOCUMENTS

| | | | |
|---|---|---|---|
| 3,779,237 | 12/1973 | Goeltz et al. | 128/710 |
| 3,922,686 | 11/1975 | France et al. | 128/696 |
| 4,424,815 | 1/1984 | Kuntz | 346/33 ME |
| 4,528,987 | 7/1985 | Slocum | 128/696 |

Primary Examiner—William E. Kamm
Assistant Examiner—Timothy Keegan
Attorney, Agent, or Firm—Cushman, Darby & Cushman

[57] ABSTRACT

A system and method for minimizing time-base fluctuations in playing back an electrocardiogram recorded on one track of a multi-track magnetic tape with reference clock signals recorded on another track. A sampling circuit samples the recorded electrocardiogram in response to sampling pulses produced in response to the recorded reference clock signals, and the sampled electrocardiogram is stored in a memory. The stored signal is then read in response to timing pulses produced by a generator. The phase difference between the sampling and timing pulses is detected and maintained constant.

11 Claims, 2 Drawing Figures

ELECTROCARDIOGRAM PLAYBACK SYSTEM AND METHOD

BACKGROUND OF THE INVENTION

This invention relates to an electrocardiogram playback system for obtaining an accurate electrocardiogram waveform, particularly one with less time-base fluctuation.

Holter recorder systems are conventionally in use for recording and playing back electrocardiograms. In that system, a portable electrocardiogram recorder/playback unit is used to obtain analytical electrocardiogram waveforms by recording electrocardiogram signals on a magnetic tape for hours at low speed and later playing back the tape at high speed. Although Holter systems are convenient, time-base fluctuation in Holter systems must be held to about 3% or less to accurately analyze the reproduced electrocardiogram waveform.

The playback signal time-base fluctuation often becomes large, however, when the low-speed recording alone is simply played back at high speed. In consequence, a reference clock signal is simulataneously recorded on another track in the conventional Holter recorder system while an electrocardiogram signal is being recorded. The reference clock signal is then used to servo-control a capstan-rotating mechanism of the playback unit when the electrocardiogram is reproduced. Notwithstanding, the playback signal time-base fluctuation remains in the neighborhood of 10%, which is still too high for accurate analysis of an electrocardiogram waveform.

In video technology time-base collectors are used for correcting playback signal time-base fluctuations. The time-base collector corrects the video signal time base (jitter) by extracting a clock signal with a horizontal or vertical synchronizing signal as a time reference. The time-base collector is indeed an ingenious device utilizing the special characteristics of a video signal, namely a discontinuous waveform in which a synchronizing signal can be inserted.

Since the electrocardiogram signal is a continuous analog signal, however, it is difficult to insert a signal equivalent to the synchronizing signal into the electrocardiogram signal, and therefore a time-base collector cannot be easily employed for correcting the time-base fluctuation in the electrocardiogram playback waveform.

As another possibility for correcting the playback signal time-base fluctuation, the continuous electrocardiogram signal could be divided at proper intervals and compressed in terms of a time-base. A synchronizing signal can then be inserted into the time gap resulting from compression, and recording is then carried out. At the time of playback, the time base is corrected with the synchronizing signal as a reference signal. However, this time-base compression method necessitates more circuitry which precludes use in an electrocardiogram signal system employing a compact, lightweight recorder like the Holter recorder.

Another way of dealing with the playback signal time-base fluctuation, is found in the field of digital recording technology, such as CD (Compact Disk), DAT (Digital Audio Tape). Time-base fluctuation in such a transmission system is minimized by converting an input signal into a digital signal and transmitting the digital signal to a playback unit. This method, as in the case of the above mentioned time-base compression method, also causes the device to become too complex and large to be used in electrocardiogram signal playback

SUMMARY OF THE INVENTION

In view of the above problems, an object of the present invention is to provide an electrocardiogram playback system with less time-base fluctuation, but without increasing circuit complexity and size of the recording unit.

According to the present invention, an electrocardiogram waveform with less time-base fluctuation can be reproduced by recording a reference clock signal on another track simultaneously while an electrocardiogram signal is recorded on a magnetic tape, causing a memory unit to store the electrocardiogram signal using a sampling pulse derived from the reference clock signal at the time of playback, reading out the electrocardiogram signal with a timing pulse for reading at a constant speed and controlling the playback magnetic tape feeding speed or the period of the timing pulse so as to maintain constant the phase difference between the sampling and timing pulses.

To accomplish the above object, the electrocardiogram playback system according to the present invention includes a plurality of track heads for simultaneously reading an electrocardiogram signal obtained from an electrocardiogram electrode and a reference clock signal both recorded by an electrocardiogram recorder for hours on different tracks of a magnetic tape. A sampling circuit samples the recorded electrocardiogram in response to sampling pulses produced in response to the recorded reference clock signals, and the sampled electrocardiogram is stored in as memory. The stored signal is then read in response to timing pulses produced by a generator. The phase difference between the sampling and timing pulses is detected and maintained constant.

PREFERRED EMBODIMENT OF THE INVENTION

Figure 1:
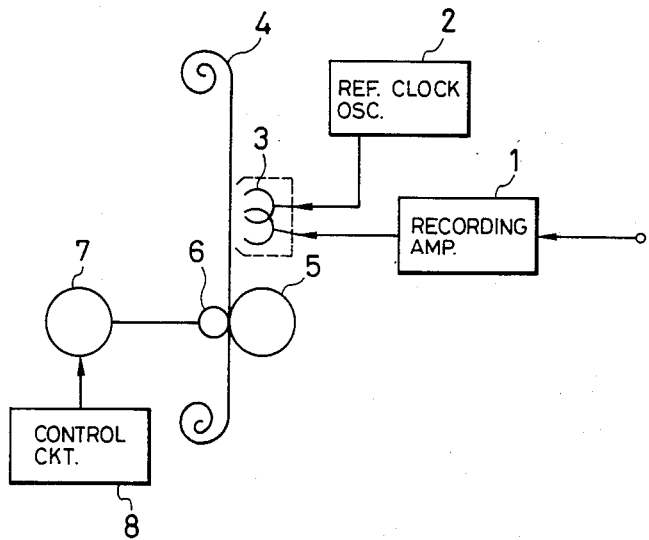
FIG. 1 is a block diagram showing a recording system for a electrocardiogram playback system embodying the present invention.
Figure 2:
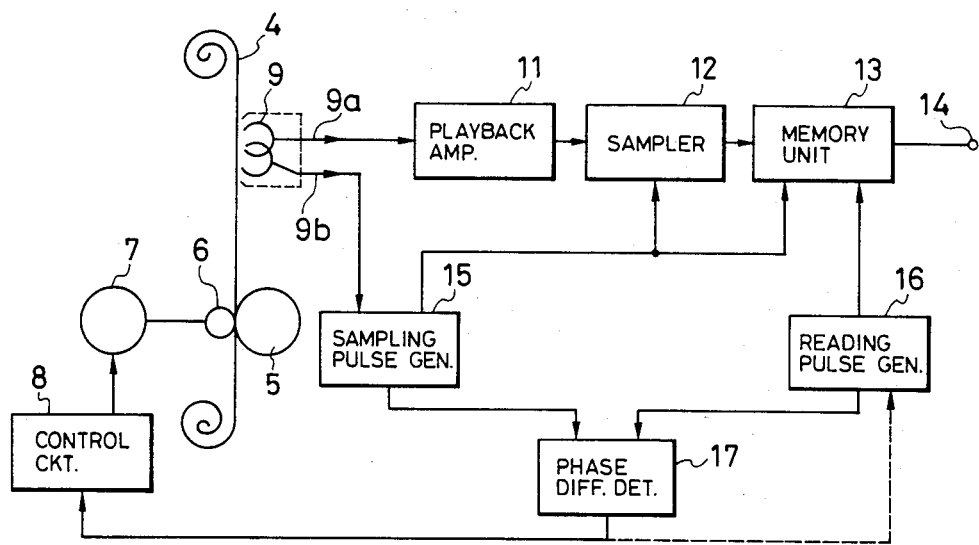
FIG. 2 is a block diagram showing a playback system of an embodiment of the present invention.

Referring now to FIGS. 1 and 2, a preferred embodiment of the present invention will be described. The recording and playback systems are integrated into a recorder according to this embodiment.

In the recording system in FIG. 1, a recording amplifier 1 amplifies an electrocardiogram signal obtained from a conventional electrocardiogram electrode (not shown). The outputs of a reference clock oscillator 2, and amplifier 1 are applied to a plurality of conventional recording heads 3 which record signals on a plurality of tracks. The clock signals and electrocardiogram signals are thus recorded on a magnetic tape 4 having a plurality of tracks. A conventional tape feed system including a pinch roller 5, a capstan 6, a capstan motor 7 and a capstan motor control circuit 8 drive tape 4.

The playback system in FIG. 2, likewise includes a plurality of playback track heads 9 with, on the electrocardiogram signal side, an output terminal 9a to which a playback amplifier 11, a sampler 12 and a memory unit 13 are serially connected. An output terminal 14 for an electrocardiogram playback signal with the time-base corrected is provided from memory unit 13.

A sampling pulse generator 15 for forming a sampling pulse from the reproduced reference clock signal is connected to the output terminal 9b, on the reference clock signal side, of the track heads 9. The output of the sampling pulse generator 15 is also connected to the sampler 12 and the memory unit 13.

The electrocardiogram signal amplified by the sampler 12 is sampled with the sampling pulse before being stored in memory unit 13.

The timing pulse output terminal of a reading pulse generator 16 is connected to the memory unit 13. Moreover, the sampling pulse generator 15 and the reading pulse generator 16 are connected to a phase difference detector 17, whose output terminal is connected to the capstan motor control circuit 8.

The output of the phase difference detector 17 is supplied to the capstan control circuit 8 when the latter is actuated as a playback for controlling the magnetic tape feed speed.

The operation of the electrocardiogram playback system will now be described.

When an electrocardiogram signal is recorded, a magnetic tape 4 having a plurality of tracks is driven by the tape feed mechanism of capstan 6 and pinch roller 5 at a predetermined low speed. The electrocardiogram signal amplified by the recording amplifier 1 and the reference clock signal produced by reference clock oscillator 2 are separately recorded on different tracks.

At the time of playback, the magnetic tape 4 is run at a predetermined analytical high speed under the control of the capstan motor control circuit 8, whereby the electrocardiogram signal and the reference clock signal are played back by the track heads 9.

The reference clock thus reproduced is supplied to the sampling pulse generator 15 and a sampling pulse is formed from the reference clock signal and supplied to the sampler 12 and the memory unit 13. Moreover, the electrocardiogram signal thus reproduced is amplified by the playback amplifier 11, sent to the sampler 12 where the signal is sampled with the sampling pulse and then stored in the memory unit 13. The electrocardiogram signal thus stored is read out of the memory unit 13 at output terminal 14 by the constant-speed timing pulse produced by the reading pulse generator 16 so that the desired electrocardiogram waveform is generated.

The sampling pulses produced by the sampling pulse generator 15 and the timing pulses produced by the reading pulse generator 16 are supplied to the phase difference detector 17 and the phase difference between the pulses, i.e., the phase difference between the position wherein the electrocardiogram signal is written into the memory unit 13 and the position wherein the signal is read out, is detected. The phase difference output thus detected is sent to the capstan motor control circuit 8 to control the magnetic tape 4 feed speed so as to maintain constant that phase difference. The phase difference between the sampling pulse formed from the reference clock signal and used for controlling the writing timing and the timing pulse for controlling the reading timing is so controlled as to be constant at all times. Thus, an electrocardiogram waveform with less time-base fluctuation is reproduced.

Although the control circuit maintains the output of the phase difference detector 17 constant by connecting the output terminal of the phase difference detector 17 to the capstan motor control circuit 8, an electrocardiogram waveform with less time-base fluctuation may be reproduced instead by connecting the output terminal of the phase difference detector 17 to the pulse generator 16 as shown by a dash line in FIG. 2 thereby controlling the period of the timing pulse produced by the reading pulse generator 16 with the output of the phase difference detector 17 to make constant the value of the output of the phase difference detector 17. Thus is formed a control circuit for making constant the output of the phase difference detector by the control circuit within the reading pulse generator 16.

An electrocardiogram playback system may be also useful for playing back time data recorded simultaneously with an electrocardiogram signal. A self-clocking digital signal, other than a square or sine wave, may be used as a reference clock and recorded on the magnetic tape, whereby time data and the like can be transmitted to the playback system by converting the time data into a digital signal and modulating in a self-clocking form through bi-phase modulation. The reference clock signal is taken out of the digital signal train at the time of playback and used as a reference signal for forming sampling pulses. In the case of bi-phase modulation, the transmission data quantity of a digital signal is assumed 1Kbpi–5Kbpi (bpi=number of transmission bits per inch) in view of the extractable reference clock signal and quality.

As set forth above, the time-base fluctuation in the playback electrocardiogram waveform can effectively be limited to as low as 3%, which is essential to accurate analysis, by recording the reference clock signal simultaneously with the electrocardiogram signal at the time of recording, causing the memory unit to store the electrocardiogram signal with the sampling pulses formed from the reference clock signal at the time of playback, subsequently reading the electrocardiogram signal with the timing pulse, detecting the phase difference between the position wherein the electrocardiogram signal is written into the memory unit and the position wherein the signal is read out and maintaining the phase difference constant at all times. Since the recording system needs to be equipped with the reference clock generator only, moreover, the recording unit remains simple unlike conventional means requiring time-base compression means for correcting time-base fluctuation.

What is claimed:

1. An electrocardiogram playback system comprising:
    a plurality of track heads for simultaneously reading an electrocardiogram recorded on one track of a multi-track magnetic tape and reference clock signals recorded on another track of said tape;
    means for driving said tape past said heads;
    a sampling pulse generator connected to said heads for producing sampling pulses in response to the recorded reference clock signals;
    sampling means for sampling the recorded electrocardiogram in response to said sampling pulses;
    memory means for storing the sampled electrocardiogram;
    reading pulse generator means for producing a timing pulse for reading said sampled electrocardiogram from said memory means;
    a phase detector means for detecting the phase between said sampling pulses and said timing pulses; and control circuit means for maintaining said phase difference constant.

2. A system as in claim 1 wherein said control circuit means controls said driving means to maintain said phase difference constant.

3. A system as in claim 1 wherein the output of said phase detector means is connected to said reading pulse generator means to control the period of said timing pulses.

4. A system as in claim 1 further including a playback amplifier connected between said heads and said sampling means.

5. A method of playing back an electrocardiogram recorded on one track of a multi-track magnetic tape and reference clock signals recorded on another track of said tape, comprising the steps of:
 driving said tape past a plurality of track heads;
 producing sampling pulses in response to detection by one head of the recorded reference clock signals;
 sampling the recorded electrocardiogram detected by another head in response to said sampling pulses;
 storing the sampled electrocardiogram;
 producing timing pulses for reading said sampled electrocardiogram from said memory means;
 detecting the phase difference between said sampling pulses and said timing pulses; and
 maintaining said phase difference constant.

6. A method of recording and playing back an electrocardiogram comprising the steps of:
 recording said electrocardiogram on one track of a multi-track magnetic tape and recording a reference clock signal on another track of said tape;
 driving said tape past a plurality of track heads;
 producing sampling pulses in response to the detection by one of said heads of recorded reference clock signals;
 sampling the recorded electrocardiogram in response to said sampling pulses;
 storing the sampled electrocardiogram;
 producing timing pulses for reading said sampled electrocardiogram from said memory means;
 detecting the phase between said sampling pulses and said timing pulses; and
 maintaining said phase difference constant.

7. A method as in claim 6 wherein said reference clock signal is a digital self-clocking digital signal.

8. An electrocardiogram recording/playback system comprising:
 means for recording an electrocardiogram on one track of a multi-track magnetic tape and reference clock signals on another track of said tape;
 means for driving said tape past said heads;
 a plurality of track heads or simultaneously reading an electrocardiogram on said one track of said multi-track magnetic tape and reference clock signals on said another track of said tape;
 a sampling pulse generator connected to said heads for producing sampling pulses in response to said recorded reference clocks;
 sampling means for sampling the recorded electrocardiogram in response to said sampling pulses;
 memory means for storing the sampled electrocardiogram;
 reading pulse gnerator means for producing timing pulse for reading said sampled electrocardiogram from said memory means;
 phase detector means for detecting the phase between said sampling pulses and said timing pulses; and
 control circuit for maintaining said phase difference constant.

9. A system as in claim 8 wherein said control circuit means controls said driving means to maintain said phase difference constant.

10. A system as in claim 8 wherein the output of said phase detector means is connected to said reading pulse generator means to control the period of said timing pulses.

11. A system as in claim 8 further including a playback amplifier connected between said heads and said sampling means.

* * * * *